(12) United States Patent
Elhofy et al.

(10) Patent No.: US 9,637,721 B2
(45) Date of Patent: May 2, 2017

(54) MEDIA FOR CELL CULTURE

(71) Applicant: Essential Pharmaceuticals, LLC, Ewing, NJ (US)

(72) Inventors: Adam Elhofy, Chicago, IL (US); Allan Weber, Robbinsville, NJ (US)

(73) Assignee: BIO-ESS LABORATORIES, LLC., Princeton, NJ (US)

( * ) Notice: Subject to any disclaimer, the term of this patent is extended or adjusted under 35 U.S.C. 154(b) by 0 days.

(21) Appl. No.: 14/577,414

(22) Filed: Dec. 19, 2014

(65) Prior Publication Data
US 2015/0175956 A1    Jun. 25, 2015

Related U.S. Application Data (60) Provisional application No. 61/918,833, filed on Dec. 20, 2013.

(51) Int. Cl.
    *C12N 5/00* (2006.01)

(52) U.S. Cl.
    CPC ........ *C12N 5/0037* (2013.01); *C12N 2500/24* (2013.01); *C12N 2500/35* (2013.01); *C12N 2500/46* (2013.01)

(58) Field of Classification Search
    None
    See application file for complete search history.

(56) References Cited

U.S. PATENT DOCUMENTS

| | | |
|---|---|---|
| 4,560,655 A | 12/1985 | Baker |
| 4,721,676 A | 1/1988 | Zeikus |
| 5,324,666 A | 6/1994 | Siepmann et al. |
| 5,952,198 A | 9/1999 | Chan |
| 5,985,538 A | 11/1999 | Stachecki |
| 6,048,728 A | 4/2000 | Inlow et al. |
| 6,103,529 A | 8/2000 | Price et al. |
| 6,162,643 A | 12/2000 | Wille, Jr. |
| 6,217,899 B1 | 4/2001 | Benameur et al. |
| 7,112,576 B1 | 9/2006 | Hubel |
| 7,220,538 B2 * | 5/2007 | Fischer .................... A01N 1/02 435/1.1 |
| 7,709,229 B2 | 5/2010 | Casatorres Hernandez et al. |

(Continued)

FOREIGN PATENT DOCUMENTS

| | | |
|---|---|---|
| EP | 2243827 A1 | 10/2010 |
| WO | WO-0008952 A1 | 2/2000 |

(Continued)

OTHER PUBLICATIONS

Pathak et al., IOSR J. Pharm. Biol. Sci. 1(1): 50-53 (May-Jun. 2012).*

(Continued)

*Primary Examiner* — Erin M Bowers
(74) *Attorney, Agent, or Firm* — Marshall, Gerstein & Borun LLP (57) ABSTRACT

The present disclosure relates, in general, to a media, e.g., a serum replacement, media supplement, complete media or cryopreservation media, comprising a base physiological buffer and liposomes comprising cholesterol, phosphatidylcholine and fatty acids. It is contemplated that media provides advantages to improve cell growth in culture compared to cells cultured not using the serum replacement described herein.

8 Claims, 4 Drawing Sheets

Splenocyte Proliferation after restimulation (56) References Cited

U.S. PATENT DOCUMENTS

| | | | |
|---|---|---|---|
| 7,935,478 | B2 | 5/2011 | Natan et al. |
| 2002/0031825 | A1 | 3/2002 | Bertheussen |
| 2005/0037492 | A1 | 2/2005 | Xu et al. |
| 2006/0188867 | A1 | 8/2006 | Acker et al. |
| 2008/0113433 | A1 | 5/2008 | Robins et al. |
| 2008/0299540 | A1 | 12/2008 | Ince et al. |
| 2010/0021531 | A1 | 1/2010 | Yoshino et al. |
| 2013/0130373 | A1 | 5/2013 | Elhofy et al. |

FOREIGN PATENT DOCUMENTS

| | | |
|---|---|---|
| WO | WO-0111011 A2 | 2/2001 |
| WO | WO-03064598 A2 | 8/2003 |
| WO | WO-2006004728 A2 | 1/2006 |
| WO | WO-2006/017370 A2 | 2/2006 |
| WO | WO-2006/045064 A2 | 4/2006 |
| WO | WO-2007/016366 A2 | 2/2007 |
| WO | WO-2007/071389 A1 | 6/2007 |
| WO | WO-2008/137641 A2 | 11/2008 |
| WO | WO-2009/023194 A2 | 2/2009 |

OTHER PUBLICATIONS

Bettger et al., Rapid Clonal Growth and Serial Passage of human diploid fibroblasts in a lipid-enriches synthetic medium supplemented with epidermal growth factor, insulin, an dexamethasone, *Proc. Natl. Acad. Sci. USA*, 78:5588-92 (1981).

Francoeur et al., MICROCAT: A Novel Cell Proliferation and Cytotoxicity Assay Based on WST-1, *Biochemica*, 3:19-25 (1996).

Ke et al., Cell Density Governs the Ability of Human Bronchial Epithelial Cells to REcognize Serum and Transforming Growth Factor Beta-1 as Squamous Differentiation-inducing Agents, *Am. J. Pathol.*, 137:833-43 (1990).

Keen et al., Adaptation of cholesterol-requiring NS0 mouse myeloma cells to high density growth in a fully defined protein-free and cholesterol-free culture medium, *Cytotechnology*, 17(3):203-11 (1995).

Lichtenberg et al., Liposomes: preparation, characterization, and preservation, *Methods Biochem. Anal.*, 33:337-462 (1988).

McRae et al., Functional Evidence for Epitope Spreading in the Relapsing Pathology of Experimental Autoimmune Encephalomyelitis, *J. Exp. Med.*, 182(1):75-85 (1995).

Neuzil et al., Vitamin E analogues as inducers of apoptosis: implications for their potential antineoplastic role, *Redox. Rep.*, 6(3):143-51 (2001). $.

Pei et al., Serum-free culture of rhesus monkey embryonic stem cells, *Arch. Androl.*, 49(5):331-42 (2003).

Spens et al., Defined protein-free NS0 myeloma cell cultures: stimulation of proliferation by conditioned medium factors, *Biotechnol. Prog.*, 21:87-95 (2005).

Sylvester et al., Vitamin E inhibition of normal mammary epithelial cell growth is associated with a reduction in protein kinase C(alpha) activation, *Cell Prolif.*, 34(6):347-57 (2001).

Veldhoen et al., Signals mediated by transforming growth factor-β initiate autoimmune encephalomyelitis, but chronic inflammation is needed to sustain disease, *Nat Immunol.*, 7(11):1151-6 (2006).

Wolterbeek et al., Optimization, application, and interpretation of lactate dehydrogenase measurements in microwell determination of cell number and toxicity, *Assay Drug Dev. Technol.*, 3:675-82 (2005).

International search report issued in connection with PCT/US2014/071388, dated Apr. 1, 2015.

\* cited by examiner

MEDIA FOR CELL CULTURE

The present application claims the priority benefit of U.S. Provisional Patent Application No. 61/918,833, filed Dec. 20, 2013, herein incorporated by reference in its entirety.

FIELD OF THE INVENTION

The present invention relates, in general, to a cell culture media composition, e.g., a serum replacement, complete media or media supplement, comprising thermodynamically stable liposomes and a liquid base mix for culturing cells in a serum-free environment. It is contemplated that the liposomes comprise cholesterol and phosphatidylcholine and fatty acids. Also contemplated is a cryopreservation media comprising liposomes for use in preserving cells during freezing.

BACKGROUND

Culture of cells, e.g., mammalian cells or insect cells, for in vitro experiments or ex vivo culture for administration to a human or animal is an important tool for the study and treatment of human diseases. Cell culture is widely used for the production of various biologically active products, such as viral vaccines, monoclonal antibodies, polypeptide growth factors, hormones, enzymes and tumor specific antigens. However, many of the media or methods used to culture the cells comprise components that can have negative effects on cell growth and/or maintenance of an undifferentiated cell culture. For example, mammalian or insect cell culture media is often supplemented with blood-derived serum, such as fetal calf serum (FCS) or fetal bovine serum (FBS) in order to provide growth factors, carrier proteins, attachment and spreading factors, nutrients and trace elements that promote proliferation and growth of cells in culture. However, the factors found in FCS or FBS, such as transforming growth factor (TGF) beta or retinoic acid, can promote differentiation of certain cell types (Ke et al., Am J Pathol. 137:833-43, 1990) or initiate unintended downstream signaling in the cells that promotes unwanted cellular activity in culture (Veldhoen et al., Nat Immunol. 7(11): 1151-6, 2006).

The uncharacterized nature of the serum composition and lot-to-lot variation of the serum make use of a serum replacement and culture in serum-free media desirable (Pei et al., Arch Androl. 49(5):331-42, 2003). Moreover, for cells, recombinant proteins or vaccines for therapeutic use that are grown in cell culture, the addition of animal-derived components is undesirable due to potential virus contamination and/or to the potential immunogenic effect of the animal proteins when administered to humans.

Serum replacements have been developed in attempts to minimize the effects of FCS on cell culture, as well as minimize the amount of animal protein used for culture of human cells. Serum replacement, such as KNOCKOUT™ serum replacement (Invitrogen, Carlsbad, Calif.), is termed a chemically defined culture medium, lacking serum and containing essential nutrients and other proteins for cell growth. KNOCKOUT SR™ cannot be used as a replacement for FBS in the plating of feeder cells due to the lack of attachment factors, which results in inadequate cell attachment in this formulation. PC-1™ serum free media (Lonza, Walkersville, Md.) is a low-protein, serum-free medium formulated in a specially modified DMEM/F12 media base and contains a complete HEPES buffering system with known amounts of insulin, transferrin, fatty acids and proprietary proteins.

Cellgro COMPLETE™ (Cellgro, Manassas, Va.) is a serum-free, low-protein culture media based on a mix of DMEM/F12, RPMI 1640 and McCoy's 5A base mediums. Cellgro COMPLETE™ does not contain insulin, transferrin, cholesterol, growth or attachment factors, but comprises a mixture of trace elements and high molecular weight carbohydrates, extra vitamins, a non-animal protein source, and bovine serum albumin.

Serum-free medias are also described in International Patent Publication Nos. WO2009023194, WO2008137641, WO2006017370, WO2001011011, WO2007071389, WO2007016366, WO2006045064, WO2003064598, WO2001011011, US Patent Publication Nos. US20050037492, US20080113433, US20080299540, U.S. Pat. Nos. 4,560,655, 5,324,666, 6,162,643, 6,103,529, 6,048,728, 7,709,229 and European Patent Application No. EP2243827.

U.S. Pat. No. 7,220,538 describes a cell culture media comprising lipophilic nanoparticles and base nutritive media.

SUMMARY OF THE INVENTION

The present disclosure provides a media comprising a base physiological buffer liquid mix and liposomes comprising cholesterol, phosphatidylcholine and fatty acids which can be used as a serum replacement, complete media or media supplement. The media is useful for promoting viability, growth and proliferation of primary cells or cell lines in cell culture, wherein the media comprises liposomes with a lipid profile conducive to cell maintenance and growth. Also contemplated is a cryopreservation media comprising liposomes.

In various embodiments, the disclosure provides a media for use with cells in suspension or in adherent culture, the media comprising a base physiological buffer liquid mix and (a) liposomes comprising cholesterol, phosphatidylcholine and fatty acids, wherein the liposome is in an amount such that the final concentration of cholesterol in a cell suspension or adherent culture is from 1 to 20 mg/L, and wherein the final concentration of phosphatidylcholine in a cell suspension or adherent culture is from 100-1000 mg/L; or (b) pectin; or (a) and (b).

In various embodiments, the liposomes comprise lipids, fatty acids, sterols and/or free fatty acids. Exemplary fatty acids include, but are not limited to, linolenic acid, linoleic acid, myristic acid, oleic acid myristoleic acid, palmitoleic acid, sapienic acid, elaidic acid, vaccenic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid and cerotic acid. In various embodiments, the liposomes comprise one or more fatty acids selected from the group consisting of linolenic acid, linoleic acid, myristic acid and oleic acid.

In various embodiments, the liposome further comprises ethanolamine and polysorbate. In various embodiments, the liposome comprises an antioxidant.

In various embodiments, the base physiological buffer liquid mix comprises one or more of an organic salt, an inorganic salt, a buffer, an iron source or iron transporter, glycerol, an amino acid, a vitamin, a sugar, and trace elements. Optionally, the base physiological buffer liquid mix comprises an antioxidant.

In various embodiments, the iron source or iron transporter is selected from the group consisting of transferrin, lactoferrin, ferrous sulfate, ferrous citrate, ferric citrate, ferric nitrate, ferric sulfate, ferric ammonium citrate, ferric ammonium oxalate, ferric ammonium fumarate, ferric ammonium malate and ferric ammonium succinate.

In various embodiments, the base physiological buffer liquid mix comprises one or more amino acids selected from the group consisting of glycine, L-alanine, L-arginine, L-asparagine, L-aspartic acid, L-citrulline, L-cysteine hydrochloride, L-cystine, L-glutamic acid, L-glutamine, L-histidine, L-isoleucine, L-leucine, L-lysine, L-methionine, L-ornithine, L-phenylalanine, L-proline, L-serine, L-threonine, L-tryptophan, L-tyrosine, and L-valine.

In various embodiments, the base physiological buffer liquid mix comprises one or more organic or inorganic salts selected from the group consisting of potassium phosphate, calcium chloride (anhydrous), cupric sulfate, ferric nitrate, ferric sulfate, magnesium chloride (anhydrous), magnesium sulfate (anhydrous), potassium chloride, sodium bicarbonate, sodium chloride, sodium phosphate dibasic anhydrous, sodium phosphate monobasic, tin chloride, zinc sulfate and sodium bicarbonate.

In various embodiments, the liposome or the base physiological buffer liquid mix comprises one or more antioxidants. Exemplary antioxidants include, but are not limited to tocopherols, tocotrienols, alpha-tocopherol, beta-tocopherol, gamma-tocopherol, delta-tocopherol, alpha-tocotrienol, beta-tocotrienol, alpha-tocopherolquinone, Trolox (6-hydroxy-2,5,7,8-tetramethylchroman-2-carboxylic acid), butylated hydroxyanisole (BHA), butylated hydroxytoluene (BHT), flavonoids, isoflavones, lycopene, beta-carotene, selenium, ubiquinone, luetin, S-adenosylmethionine, glutathione, taurine, N-acetylcysteine, citric acid, L-carnitine, BHT, monothioglycerol, ascorbic acid, propyl gallate, methionine, cysteine, homocysteine, gluthatione, cystamine and cysstathionine, and glycine-glycine-histidine (tripeptide).

In various embodiments, the base physiological buffer liquid mix comprises one or more vitamins selected from the group consisting of biotin, choline chloride, D-calcium pantothenate, folic acid, niacinamide, pyridoxine hydrochloride, biboflavin, thiamine hydrochloride, vitamin B12, and i-inositol.

In various embodiments, the base physiological buffer liquid mix comprises one or more trace elements selected from the group consisting of selenium, molybdnate, chromium, cobalt, nickel, zinc, copper, manganese, barium, gallium, lithium, tin, titanium, bromium, iodine, vanadium, germanium, molybdenum, silicon, iron, fluorine, silver, rubidium, zirconium, cadmium, and aluminum. In various embodiments, the liquid mix comprises selenium and molybdnate.

In various embodiments, the media is a serum replacement, complete media, media supplement or cryopreservation media.

In various embodiments, the serum replacement, complete media or media supplement for use in cell culture comprises liposomes and base physiological buffer liquid mix. Optionally, the complete media or media supplement comprises pectin. In various embodiments, the serum replacement, complete media or media supplement further comprises a base physiological buffer liquid mix comprising one or more organic or inorganic salts, an iron donor and, optionally comprising pectin, glycerol, amino acids, vitamins, sugars, organic salts, inorganic salts, and trace elements.

In various embodiments, the disclosure also provides a serum replacement, complete media or media supplement comprising liposomes and a base physiological buffer liquid mix, wherein the liposomes comprise phosphatidylcholine, ethanolamine, linolenic acid, linoleic acid, cholesterol, and polysorbate, and the base liquid mix comprises at least one organic or inorganic salt, at least one sugar, glycerol, at least one trace element, at least one non-ionic surfactant, and at least one iron source. In various embodiments, the liposome or the base liquid mix comprises at least one antioxidant.

In various embodiments, for the serum replacement, complete media or media supplement described herein, the liposome is in an amount such that the final concentration of cholesterol in a cell suspension or adherent culture is from 1 to 20 mg/L, and wherein the final concentration of phosphatidylcholine in a cell suspension or adherent culture is from 100-1000 mg/L.

In various embodiments, the liposome comprises one or more fatty acids selected from the group consisting of linolenic acid, linoleic acid, myristic acid and oleic acid. Additional fatty acids contemplated include, but are not limited to, myristoleic acid, palmitoleic acid, sapienic acid, elaidic acid, vaccenic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid and cerotic acid.

In various embodiments, the liposome further comprises ethanolamine. In various embodiments the liposome further comprises polysorbate. It is contemplated that the polysorbate can be polysorbate 20, polysorbate 40, polysorbate 60 or polysorbate 80. Exemplary polysorbates include TWEEN® 20 and TWEEN® 80.

In various embodiments, the one or more organic or inorganic salts is selected from the group consisting of potassium phosphate, calcium chloride (anhydrous), cupric sulfate, ferric nitrate, ferric sulfate, magnesium chloride (anhydrous), magnesium sulfate (anhydrous), potassium chloride, sodium bicarbonate, sodium chloride, sodium phosphate dibasic anhydrous, sodium phosphate monobasic, tin chloride, zinc sulfate and sodium bicarbonate. In various embodiments, the liquid mix comprises sodium chloride, potassium chloride, sodium phosphate and potassium phosphate.

In various embodiments, the media further comprises an iron source or an iron transporter. In various embodiments, the iron source or iron transporter is selected from the group consisting of transferrin, lactoferrin, ferrous sulfate, ferrous citrate, ferric citrate, ferric nitrate, ferric sulfate, ferric ammonium citrate, ferric ammonium oxalate, ferric ammonium fumarate, ferric ammonium malate and ferric ammonium succinate. In various embodiments, the iron source is ferric citrate. In various embodiments, the iron transporter is transferrin.

In various embodiments, the serum replacement further comprises a copper source or copper transporter (e.g., GHK-Cu). Exemplary copper sources include, but are not limited to, copper chloride and copper sulfate.

In various embodiments, the liquid mix comprises one or more non-ionic surfactants selected from the group consisting of Pluronic-68 (F68 pastille), Pluronic-128, sorbitan, polysorbate and block copolymers. In various embodiments, the non-ionic surfactant is Pluronic-68 (F68 pastille).

In various embodiments, the media provides that the final concentration of glycerol in cell culture, e.g., a cell suspension or adherent culture, is from about 2 uls to 0.5 mL/L per Liter.

In various embodiments, the media provides that the final concentration of pectin in cell culture, e.g., a cell suspension or adherent culture, is from about 0.25 to 0.5 g/L, or 25 to 500 mg/L.

In various embodiments, the media provides that the final concentration of selenium in cell culture, e.g., a cell suspension or adherent culture, is from about 0.005 to 0.050 mg/L.

In various embodiments, also contemplated is a serum replacement, wherein the final concentration of cholesterol from the liposome in the serum replacement is from about 10 to 200 mg/L, and the final concentration of the phosphotidylcholine from the liposome in the serum replacement is from about 50 mg to 1 g/L, or from about 1000 mg to 10 g/L.

In various embodiments, the disclosure provides a complete media wherein the concentration of cholesterol from the liposome in the complete media is from about 1 to 20 mg/L and the concentration of the phosphotidylcholine from the liposome in the complete media is from about 100 mg to 1000 mg/L.

In various embodiments, the disclosure provides a media supplement wherein the concentration of cholesterol from the liposome in the media supplement is from about 100 to 2000 mg/L or more, and the concentration of the phosphotidylcholine from the liposome in the media supplement is from about 10 g to 100 g/L.

In various embodiments, the disclosure provides a cryopreservation media, wherein the final concentration of cholesterol from the liposome in the cryopreservation media is from about 10 to 200 mg/L and the final concentration of the phosphotidylcholine from the liposome in the cryopreservation media is from about 1000 mg to 10 g/L.

In various embodiments, the liposome is a nanoparticle. In various embodiments, the nanoparticle has a mean diameter ranging from about 50 to 500 nm, from about 100 nm to about 300 nm or from about 100 to 200 nm.

It is provided herein that the liposomes are thermodynamically stable. In various embodiments, the liposome is stable in aqueous solution (e.g., does not precipitate). In various embodiments the liposome is stable in aqueous solution for a period of at least 7 days, 10 days, 14 days, 21 days, 30 days, 2 months, 3 months, 6 months, or 1 year or more at 37° C., 25° C., 4° C., 0° C., or −20° C. Exemplary aqueous solutions include, but are not limited to, water, buffered saline and other balanced salt solutions, basal cell culture media and complete cell culture media.

Also provided herein is a cell cryopreservation media comprising liposomes, a base physiological buffer liquid mix, and optionally, pectin.

Also contemplated herein is a cell cryopreservation media comprising a base physiological buffer liquid mix and pectin.

In various embodiments, in the cryopreservation media, the final concentration of pectin in the cell suspension is from about 0.25 to 5 g/L, or 250 to 5000 mg/L or from about 50 mg/L to 5 g/L.

In various embodiments, a cryopreservation media described herein further comprises glycerol. In various embodiments, when using the cryopreservation media, the glycerol in cell suspension is at a final concentration of from about 0.2 to 5 mLs/L.

In various embodiments, the cryopreservation media further comprises liposomes, wherein the liposomes comprise cholesterol, phosphatidylcholine and fatty acids, wherein the liposome is in an amount such that the final concentration of cholesterol in a cell suspension is from about 10 to 200 mg/L, and wherein the final concentration of phosphatidylcholine in a cell suspension is from about 1 to 10 g/L.

In various embodiments, the cryopreservation media further comprises dimethyl sulfoxide (DMSO), wherein the DMSO is at a concentration in the cryopreservation media of less than or equal to 4%. In various embodiments, the concentration of DMSO is 4%, 3%, 2%, 1% or 0.5%.

In various embodiments, the cryopreservation media further comprises polylysine. In various embodiments, the polylysine is a modified polylysine. In various embodiments, the polylysine is epsilon-poly-L-lysine. In certain embodiments, the polylysine comprises carboxylated amino groups. In various embodiments, the polylysine is at a final concentration of about 10%, 9%, 8%, 7%, 6%, 5%, 4%, 3%, 2%, 1% or 0.5%.

In various embodiments, the serum replacement or media supplement is added to a basic media prior to cell culture. Standard basic media are known in the art and commercially available. Examples of such media include, but are not limited to, Dulbecco's Modified Eagle's Medium (DMEM), DMEM F12, Iscove's Modified Dulbecco's Medium, Ham's Nutrient mixture F-10 (Ham's F-10) or Ham's F-12, Roswell Park Memorial Institute Medium (RPMI), MCDB 131, Click's medium, McCoy's 5A Medium, Medium 199, William's Medium E, and insect media such as Grace's medium and TNM-FH.

Any of these media are optionally supplemented with salts, amino acids, vitamins, buffers, nucleotides, antibiotics, trace elements, and glucose or an equivalent energy source. Other optional supplements may also be included at appropriate concentrations that would be known to those skilled in the art. Media supplements are well-known in the art and commercially available, and are described in greater detail in the Detailed Description.

In various embodiments, it is further contemplated that the serum replacement itself comprises the elements of a base media and supplements as described above, e.g., salts, amino acids, vitamins, buffers, nucleotides, antibiotics, trace elements, antioxidants, and glucose or an equivalent energy source, such that the serum replacement is provided as a serum-free complete media.

In various embodiments, the media is animal-component free.

In various embodiments, the liposomes are loaded with a base liquid mix described herein. It is further contemplated that the liposome is loaded with other compositions beneficial in cell culture. Exemplary compositions beneficial in cell culture include, but are not limited to, buffers, iron transporters, free fatty acids, growth peptides (e.g., insulin, GHK peptide comprising gly-his-lys trimer), amino acids (essential and non-essential), vitamins, trace elements, antioxidants and/or salts.

In various embodiments, the disclosure provides a method of culturing cells comprising culturing cells in a complete media or media containing a serum replacement, or media supplement described herein.

In various embodiments, the cells are selected from the group consisting of mammalian cells and insect cells. In various embodiments, the cell is isolated from a mammalian subject. In various embodiments, the cell is a primary culture or a cell line. In various embodiments, the cell is selected from the group consisting of pluripotent stem cells, embryonic stem cells, bone marrow stromal cells, hematopoietic progenitor cells, lymphoid stem cells, myeloid stem cells, T cells, B cells, macrophages, hepatic cells, pancreatic cells, and cell lines.

Mammalian cell lines contemplated include, but are not limited to, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, a T cell line (e.g., Jurkat), a B cell line (e.g., BJAB, EW36, CA46, ST486 and MC116, Raji, Namalva and Daudi), 3T3, RIN, A549, PC12, K562, PER.C6®, SP2/0, NS-0, U20S, HT1080, L929, hybridomas, cancer cell lines, and other cell lines well-known in the art. Insect cell lines contemplated include, but are not limited to, Sf9, Sf21, HIGH FIVE™, EXPRESSF+®, S2, Tn5, TN-368, BmN, Schneider 2, D2, C6/36 and KC cells.

In various embodiments, the disclosure contemplates a method of cryopreserving cells comprising suspending cells in a cryopreservation media described herein, optionally comprising pectin, or optionally comprising liposomes, and placing the cells in an environment of less than 8° C. Exemplary temperatures below 8° C. include, but are not limited to, temperatures at or below 4° C., 0° C., −20° C., −70° C., −135° C., or in liquid nitrogen (−196° C.).

In various embodiments, the method further comprises thawing the cells and placing them in a media as described herein.

In various embodiments, at least 30% of the frozen cells remain viable upon thawing when placed in a media described herein, whether used as a serum replacement, media supplement or complete media. In various embodiments, viability of cells upon thaw is about 40%, 50%, 60%, 65%, 70%, 75%, 80% or higher.

In one embodiment, the media (serum replacement, media supplement, complete media or cryopreservation media) is packaged in a volume of 10 ml, 50 ml, 100 ml, 500 ml or 1 L. In a related embodiment, the serum replacement, media supplement or cryopreservation media is packaged in a 1×, 5×, 10× or 20× solution.

Also provided is a method of making the liposomes described herein. In various embodiments, the process for making the liposome comprises dissolving the desired amount of cholesterol in a non-methanol or non-chloroform solution. In various embodiments, the cholesterol is dissolved in a liquid phospholipid solution. In various embodiments the cholesterol is mixed at room temperature in non-methanol or non-chloroform solution or heated in non-methanol or non-chloroform solution until the cholesterol is in solution. The solution can be heated to about 35°, 40°, 45°, 50°, 55° or 60° C., and not more than 80° C. Once in solution, the following compositions are added to the cholesterol composition and mixed: polysorbate, ethanolamine and fatty acids. The final mixture is stored at 4° C., 0° C., or −20° C. Optionally, the cholesterol solution is mixed prior to addition of the remaining compounds.

In various embodiments, it is contemplated that certain of the media compositions or liposome compositions as described herein promote improved culture of cells, e.g., increased cell growth, cell viability or increased expression of recombinant protein, compared to media or liposome compositions comprising a different set of components. It is contemplated that those media or liposome compositions promoting improved culture of cells are used for further experimentation.

It is understood that each feature or embodiment, or combination, described herein is a non-limiting, illustrative example of any of the aspects of the invention and, as such, is meant to be combinable with any other feature or embodiment, or combination, described herein. Each of these types of embodiments is a non-limiting example of a feature that is intended to be combined with any other feature, or combination of features, described herein without having to list every possible combination. Such features or combinations of features apply to any of the aspects of the invention. Where examples of values falling within ranges are disclosed, any of these examples are contemplated as possible endpoints of a range, any and all numeric values between such endpoints are contemplated, and any and all combinations of upper and lower endpoints are envisioned.

DETAILED DESCRIPTION

The present disclosure provides a media comprising a base physiological buffer liquid mix and liposomes comprising cholesterol, phosphatidylcholine and fatty acids, where the media can be a serum replacement, complete media or media supplement composition, for use in culture of cells in vitro in order to provide growth of cells comparable to growth in fetal bovine serum (FBS) without the nonspecific side effects FBS contributes to cell physiology. The serum replacement, complete media or media supplement provides a liposome comprising cholesterol and phosphatidylcholine in a physiologically relevant concentration in combination with fatty acids such that the liposomes in the serum replacement, complete media or media supplement provide an environment to cells similar to plasma membranes. Optionally, the complete media, serum replacement, or media supplement comprises pectin. Also provided is a cryopreservation media comprising liposomes and/or pectin. The media (serum replacement, complete media, media supplement or cryopreservation media) composition herein provides advantages over culture of cells in media containing FBS or in serum-free media.

As used in the specification and the appended claims, the indefinite articles "a" and "an" and the definite article "the" include plural as well as singular referents unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range.

As used herein, a "media" or "cell culture media" refers to an aqueous based solution that provides for the growth, viability, or storage of cells. A media as contemplated herein can be supplemented with nutrients as described in the Detailed Description to promote the desired cellular activity, such as cell viability, growth, proliferation, differentiation of the cells cultured in the media. A media as used herein includes a serum replacement, media supplement, complete media or cryopreservation media.

As used herein "serum replacement" or "serum replacement media" refers to a composition that can be used in conjunction with a basal media or as a complete media in order to promote cell growth and survival in culture. In various embodiments, serum replacement is used in basal or complete media as a replacement for any serum that is characteristically added to media for culture of cells in vitro. It is contemplated that the serum replacement comprises proteins and other factors for growth and survival of cells in culture. In various embodiments, the serum replacement is added to a basal media prior to use in cell culture. It is further contemplated that, in various embodiments, a serum replacement may comprise a base media and base nutrients such as salts, amino acids, vitamins, trace elements, antioxidants, and the like, such that the serum replacement is useful as a serum-free complete media for cell culture.

As used herein a "basal media", "base media", "base medium" or "base nutritive media" refers to a basal salt nutrient or an aqueous solution of salts and other elements that provide cells with water and certain bulk inorganic ions essential for normal cell metabolism and maintains intra- and extra-cellular osmotic balance. In various embodiments, a base media comprises at least one carbohydrate as an energy source, and/or a buffering system to maintain the medium within the physiological pH range. Examples of commercially available basal media include, but are not limited to, phosphate buffered saline (PBS), Dulbecco's Modified Eagle's Medium (DMEM), Minimal Essential Medium (MEM), Basal Medium Eagle (BME), RPMI 1640, Ham's F-10, Ham's F-12, α-Minimal Essential Medium (αMEM), Glasgow's Minimal Essential Medium (G-MEM), Iscove's Modified Dulbecco's Medium, or a general purpose media modified for use with pluripotent cells, such as X-VIVO (Lonza) or a hematopoeitic base media. A base media can be supplemented with nutrients as described in greater detail in the Detailed Description.

As used herein, a "complete media" refers to basal medium further comprising added supplements, such as growth factors, hormones, proteins, serum or serum replacement, trace elements, sugars, antibiotics, antioxidants, etc., that can contribute to cell growth. For example, a commercially available complete media comprises supplements such as ethanolamine, glutathione (reduced), ascorbic acid phosphate, insulin, human transferrin, a lipid-rich bovine serum albumin, trace salts, sodium selenite, ammonium matavanadate, cupric sulfate and manganous chloride (DMEM ADVANCED™ Media, Life Technologies).

As used herein, "media supplement" refers to an agent or composition that is added to base media prior to culture of cells. A media supplement can be an agent that is beneficial to cell growth in culture, such as growth factors, hormones, proteins, serum or serum replacement, trace elements, sugars, antibiotics, antioxidants, etc. Typically a media supplement is a concentrated solution of the desired supplement to be diluted into a complete or base media to reach the appropriate final concentration for cell culture.

As used herein a "cryopreservation media" refers to a culture media useful for storing or freezing cells in suspension at a temperature at or below 8° C., including temperatures at or below 4° C., 0° C., −20° C., −70° C., −135° C., or in liquid nitrogen (−196° C.).

As used herein "pectin" refers to a structural heteropolysaccharide derived from plant cells walls, having a molecular weight from 30,000 Daltons (Da) to 250,000 Da. Pectin is composed primarily of α-1-4 linked galacturonic acid residues. In certain embodiments, the pectin is esterified, e.g., having 55%, 60%, 65%, 70%, 75% or greater esterification, and can be high- or low-ester pectin. In various embodiments, the pectin is calcium sensitive. Calcium sensitive pectin is able to interact with calcium to form a gel, whereas the non-calcium sensitive pectin does not. It is contemplated that the pectin is in an acidic solution in a range of pH 4.5-6.9 or basic solution in a range of pH 7.5 to 10 depending on the type of pectin that is used. Optionally, the pectin is in a solution with a pH range of 7.0-7.4. Pectins for use at the different pH levels can be determined using the general knowledge and skill in the field, and the pectin used at the desired pH level is influenced by the level of esterification or calcium sensitivity of the pectin.

Pectin is supplied by a commercial source and can be from any plant having pectin, such as, pears, apples, guavas, quince, plums, gooseberries, oranges and other citrus fruits, cherries, grapes and strawberries. Pectin compositions having various degrees of esterification (methylation) and calcium sensitivity are described in WO 2000008952, herein incorporated by reference.

As used herein, "liposome" refers to a closed structure comprising an outer lipid bi- or multi-layer membrane surrounding an internal aqueous space. Liposomes may be multi-laminar or unilaminar. The liposome is contemplated to range in size from 5 to 10 µM in diameter to nanoparticle size. In certain embodiments, the liposome nanoparticle is from about 50 to 500 nm, from about 100 nm to 300 nm or from about 100 to 200 nm in diameter.

As used herein a "liquid base mix" or "base physiological buffer liquid mix" refers to the base liquid solution of the serum replacement or media supplement into which the liposomes are suspended to complete the cell culture media composition. In various embodiments, it is further contemplated that the liquid base mix is loaded into the liposomes such that the liposome delivers an amount of the liquid base mix to cells when fused to/taken up by cells in cell culture. In various embodiments, it is contemplated herein that the liquid base mix or base physiological buffer liquid mix is a base media, a complete media or a physiological buffer solution, such as phosphate buffered saline (PBS) and other balanced salt solutions, which can be used in conjunction with the liposomes and/or other components herein to form a serum replacement, complete media, media supplement, or cryopreservation media.

As used herein "improved culture of cells" refers to the increased proliferation of cells, increased growth of cells, decreased cell death, or increased protein production (recombinant or endogenous) of cells when cultured using a media composition (serum replacement, complete media or media supplement) described herein compared to culture of the cells using a serum replacement not comprising liposomes or a serum-free media. Increased proliferation, increased growth and changes in cell death are measured using methods well-known in the art, including growth curve analysis, stimulation index, microscopic evaluation by trypan blue, tritiated thymidine ($^3$H) proliferation assay, MTT assay, resazurin based assays and DNA laddering analysis. Increased protein production (recombinant or endogenous) of cells is measured using techniques known in the art, including quantization of total protein or mRNA, or quantitation of levels of a particular protein of interest.

As used herein, "animal-component free" refers to a composition in which the components are not derived from animals. It is contemplated that the components are either produced recombinantly or derived from plants or other sources other than isolated directly from an animal. As used herein, animal-component free allows for recombinant production of components of the media in animal-based cell lines.

Media Compositions

Cell culture media comprising lipid components and liposomes have been described previously for use in cell culture, but with limited success. For example, Hams et al. (Proc Natl Acad Sci USA 78:5588-92, 1981) discloses culturing human fibroblasts in media comprising different lipid components, e.g., a liposome comprising cholesterol, lecithin or purified phosphatidylcholine, sphingomyelin and vitamin E. However, Hams describes that the liposomes are not stable in that they need to be made within 24 hours of use, and shows that simply using the liposomes in complete media does not promote cell growth. Spens et al. (Biotechnol Prog 21:87-95, 2005) describe culture of NS0 myeloma cells in a protein-free media further comprising cholesterol, cyclodextrin, phosphatidylcholine, vitamin E, ferric citrate, pluronic and amino acids, among other things. Spens (supra) describes that at high levels lipids precipitate out of solution (citing Keen et al., Cytotechnology. 17(3):203-11, 1995).

Methods of making liposomes are known in the art including, liquid hydration or solvent spherule preparation for making multi-laminar vesicles (having series of concentric bi-layer of lipid), sanitation, French press, solvent injection, detergent removal, reverse phase evaporation, calcium induced fusion, microfluidization or freeze-thaw methods to prepare unilaminar vesicles (having a single layer of lipids).

Liposome preparation is described in U.S. Pat. No. 7,220,538, U.S. Pat. No. 6,217,899; US Patent Publication No. 20100021531, Lichtenberg et al., Methods Biochem Anal. 33:337-462, 1988; and G. Gregoriadis: "Liposome Technology Liposome Preparation and Related Techniques," 2nd edition, Vol. I-III, CRC Press. Liposomes for pharmaceutical use have been disclosed in Mozafari, M., Liposomes, Methods and Protocols Vol. 1, Chapter 2, V. Wessing Ed. 2010, Humana Press).

In various embodiments, the disclosure provides a media for use with cells in suspension or in adherent culture, the media comprising a base physiological buffer liquid mix and (a) liposomes comprising cholesterol, phosphatidylcholine and fatty acids, wherein the liposome is in an amount such that the final concentration of cholesterol in a cell suspension or adherent culture is from 1 to 20 mg/L, and wherein the final concentration of phosphatidylcholine in a cell suspension or adherent culture is from 5-100 mg/L; or (b) pectin; or (a) and (b).

In various embodiments, the media is a serum replacement, media supplement or complete media. In various embodiments, the disclosure provides a cell cryopreservation media comprising liposomes and a base physiological buffer liquid mix, optionally comprising pectin, wherein the liposomes comprise cholesterol, phosphatidylcholine and fatty acids. In various embodiments, the liposome is in an amount such that the final concentration of cholesterol in a cell suspension is from 1 to 20 mg/L, and wherein the final concentration of phosphatidylcholine in a cell suspension is from 5-100 mg/L.

In various embodiments, the disclosure provides a cryopreservation media comprising a base physiological buffer liquid mix and pectin.

Liposomes may be multi-laminar or unilaminar. The liposome is contemplated to range in size from 5 to 10 μM in diameter to nanoparticle size. In some embodiments, the liposomes are nanoparticles. In certain embodiments, the nanoparticles have a mean diameter ranging from about 50 to 500 nm, from about 100 to about 300 nm, or from about 100 to 200 nm. Liposome size can be measured using methods known in the art, including use of a Zetasizer (Malvern Instruments, United Kingdom), which measures particle size as the average diameter value of the entire particles by the dynamic light scattering method.

In various embodiments, the liposomes comprise lipids, fatty acids, sterols and/or free fatty acids. In various embodiments, the liposomes comprise cholesterol and phosphatidylcholine, and fatty acids at concentrations that provide a more physiologically relevant milieu for cell growth. Exemplary final concentrations of the components of the liposomes in a serum replacement, complete media or media supplement composition are set out in Table 1.

TABLE 1

| Component | Media supplement | Serum Replacement | Complete Media |
|---|---|---|---|
| Cholesterol | 100 to 2000 mg/L | 10 to 200mg/L | 1 to 20 mg/L |
| Phosphatidyl-choline | 10 to 100 g/L | 50 mg/L to 1 g/L; 1000 mg to 10 g/L | 5 to 100 mg/L; 100 to 1000 mg/L |
| Fatty acids | 5 to 50 mg/L | 0.5 to 5 mg/L | 0.05 to 0.5 mg/L |
| Ethanolamine | 1 to 5 g/L | 0.5 to 50 mg/L | 5 to 500 mg/L |

In various embodiments, the serum replacement liposome comprises cholesterol at a final concentration of about 10 to 200 mg/L, 25 to 175 mg/L, 50 to 150 mg/L, 60 to 120 mg/L, 20 to 100 mg/L, 30 to 90 mg/L, 40 to 80 mg/L or 50 to 70 mg/L. In various embodiments, the serum replacement liposome comprises cholesterol at a final concentration of about 50 mg/L, about 55 mg/L, about 60 mg/L, about 65 mg/L, about 70 mg/L or about 75 mg/L.

In various embodiments, the liposome in the serum replacement is in an amount such that the final concentration of cholesterol in a cell suspension or adherent culture is from 1 to 20 mg/L, and wherein the final concentration of phosphatidylcholine in a cell suspension or adherent culture is from 5-100 mg/L or from 100 to 1000 mg/L.

In various embodiments the liposome comprises one or more fatty acids. Exemplary fatty acids, include, but are not limited to linolenic acid, linoleic acid, myristic acid, oleic acid, myristoleic acid, palmitoleic acid, sapienic acid, elaidic acid, vaccenic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid and cerotic acid. In various embodiments, the serum replacement liposome comprises fatty acids in a final concentration of about 0.5 to 5 mg/L, 0.75 to 4, 1 to 3, 0.5 to 3, 0.5 to 2, or 1 to 2 mg/L. In various embodiments, the serum replacement liposome comprises linoleic acid or linolenic acid at a final concentration of about 0.5 to 5 mg/L.

In various embodiments, the serum replacement liposome comprises ethanolamine at a final concentration of about 0.5 to 50 mg/L, 1 to 50 mg/L, 2.5 to 40 mg/L, 5 to 35 mg/L, 10 to 30 mg/L, or 15 to 25 mg/L. In various embodiments, the final concentration of ethanolamine in the serum replacement is about 1, 2.5, 5, 10, 15, 20, 25, 30, 35, 40, 45 or 50 mg/L.

In various embodiments, the liposome further comprises polysorbate. In certain embodiments the polysorbate is polysorbate 20, polysorbate 40, polysorbate 60 or polysorbate 80. Exemplary polysorbates include TWEEN® 20 or TWEEN® 80. It is contemplated that the final concentration of polysorbate in the serum replacement is between about 100 and 1000 ul/L, 200 to 800 ul/L 300 to 700 ul/L or 400 to 600 ul/L. In various embodiments, the final concentration of the polysorbate in the serum replacement is about 500 ul/L.

The final concentration described above with respect to the serum replacement composition can be used as a basis for calculating the concentration of components in either a media supplement or complete media. The final concentration of the respective components in a media supplement are 10× greater those used in the serum replacement composition. The final concentration of the respective components in a complete media is 10× less than those used in the serum replacement. Exemplary concentrations are set out in Table 1 and Table 2.

It is further contemplated that the serum replacement is used at a dilution greater than 5× or 10×. In various embodiments, the serum replacement is used at a dilution of 1:5, 1:10, 1:15, 1:20, 1:25, 1:50, 1:100, 1:200, 1:250, 1:300, 1:400, 1:500, 1:600, 1:700, 1:800, 1:900 1:1000, 1:1500 or 1:2000.

For cryopreservation media, the starting concentration of the components is the same as that used for the serum replacement media, i.e., a 10× concentration of what is used in complete media. However, the cryopreservation media is used without dilution or with only minimal dilution such that the final concentration of the components and the starting concentration are approximately equivalent. For example, in various embodiments for the cryopreservation media, the final concentration of the cholesterol in cell suspension is 10 to 200 mg/L and the final concentration of the phophatidylcholine in cell suspension is from 50 mg/L to 1 g/L, or from 1000 mg to 10 g/L.

It is contemplated that a liposome described herein is thermodynamically stable in aqueous solution despite the high concentrations of cholesterol and phosphatidylcholine present in a liposome for use in serum replacement or media supplement, and in view of long term exposure to aqueous solution when used in a complete cell culture media solution. The disclosure provides that a liposome described herein having a final concentration of components as set out in Table 1 is stable in aqueous solution (e.g., does not precipitate). In various embodiments the liposome is stable in aqueous solution for a period of at least 7 days, 10 days, 14 days, 21 days, 30 days, 2 months, 3 months, 6 months, or 1 year or more at 37° C., 25° C., 4° C., 0° C., or −20° C. Exemplary aqueous solutions include, but are not limited to, water, buffered saline and other balanced salt solutions, basal cell culture media and complete cell culture media. An advantage of the present liposome composition is that it contains physiologically relevant levels of sterols and fatty acids that provide excellent growth potentiation yet do not precipitate out of solution after several days, which has been observed in other medias comprising high levels of agents such as cholesterol and phosphatidylcholine (Spens et al., Keen et al., supra).

It is contemplated that the liquid base mix component of the media comprises one or more of pectin, glycerol, selenium and an iron source. Optionally, the liquid base mix further comprises amino acids, vitamins, sugars, inorganic salts, antioxidants and trace elements. Similar to the liposome complex described above, the liquid base mix in which the liposomes are made can be made at differing concentrations for use in serum replacement, media supplement or complete media. Exemplary final concentrations are set out in Table 2.

TABLE 2

| Component | Media supplement | Serum Replacement | Complete Media |
|---|---|---|---|
| Glycerol | 2 to 100 mL/L | 0.02 to 5 mL/L | 2 uls to 0.5 mL/L |
| Pectin | 2.5 to 50 g/L | 0.25 to 5 g/L | 25 to 500 mg/L |
| Selenium | 0.5 to 5 mg/L | 0.05 to 0.5 mg/L | 0.005 to 0.050 mg/L |

In various embodiments, the glycerol is at a final concentration in the serum replacement of about 0.02 to 5 mLs per Liter (L), or 0.05 to 4, 0.1 to 3, 0.5 to 2.5, or 1 to 2 mL/L. In various embodiments, the glycerol is at a final concentration in the serum replacement of about 0.02, 0.05, 0.1, 0.25, 0.5, 1.0, 1.5, 2, 2.5, 3, 3.5, 4, 4.5 or 5 mL/L.

In various embodiments, the pectin is in the serum replacement at a final concentration of about 0.25 to 5 g/L, 0.5 to 4 g/L, 1.5 to 3 g/L or 1 to 2 g/L. In various embodiments the pectin is at a final concentration in the serum replacement of about 0.25, 0.5, 0.75, 1, 1.5, 2, 2.5, 3, 3.5, 4, 4.5, or 5 g/L.

Exemplary inorganic salts include, but are not limited to, potassium phosphate, calcium chloride (anhydrous), cupric sulfate, ferric nitrate, ferric sulfate, magnesium chloride (anhydrous), magnesium sulfate (anhydrous), potassium chloride, sodium bicarbonate, sodium chloride, sodium phosphate dibasic anhydrous, sodium phosphate monobasic, tin chloride and zinc sulfate. Exemplary organic salts include, but are not limited to, sodium bicarbonate or HEPES.

Exemplary sugars include, but are not limited to, dextrose, glucose, lactose, galactose, fructose and multimers of these sugars.

Exemplary antioxidants include, but are not limited to tocopherols, tocotrienols, alpha-tocopherol, beta-tocopherol, gamma-tocopherol, delta-tocopherol, alpha-tocotrienol, beta-tocotrienol, alpha-tocopherolquinone, Trolox (6-hydroxy-2,5,7,8-tetramethylchroman-2-carboxylic acid), butylated hydroxyanisole (BHA), butylated hydroxytoluene (BHT), flavonoids, isoflavones, lycopene, beta-carotene, selenium, ubiquinone, luetin, S-adenosylmethionine, glutathione, taurine, N-acetylcysteine, citric acid, L-carnitine, BHT, monothioglycerol, ascorbic acid, propyl gallate, methionine, cysteine, homocysteine, gluthatione, cystamine and cysstathionine, and glycine-glycine-histidine (tripeptide).

Exemplary trace elements, include, but are not limited to, copper, iron, zinc, manganese, silicon, molybdnate, molybdenum, vanadium, nickel, tin, aluminum, silver, barium, bromine, cadmium, cobalt, chromium, calcium, divalent cations, fluorine, germanium, iodine, rubidium, zirconium, or selenium. Additional trace metals are disclosed in WO 2006/004728.

In various embodiments, the media or liquid base mix comprises an iron source or iron transporter. Exemplary iron sources include, but are not limited to, ferric and ferrous salts such as ferrous sulfate, ferrous citrate, ferric citrate, ferric nitrate, ferric sulfate, ferric ammonium compounds, such as ferric ammonium citrate, ferric ammonium oxalate, ferric ammonium fumarate, ferric ammonium malate and ferric ammonium succinate. Exemplary iron transporters include, but are not limited to, transferrin and lactoferrin.

In various embodiments, the media or liquid base mix or liposome comprises one or more elements of a base media and supplements as described above, e.g., salts, amino acids, vitamins, buffers, nucleotides, antibiotics, trace elements, antioxidants and glucose or an equivalent energy source, such that the media is capable of use as a serum-free complete media.

In various embodiments, the media or liquid base mix further comprises a copper source or copper transporter (e.g., GHK-Cu). Exemplary copper sources include, but are not limited to, copper chloride and copper sulfate.

In various embodiments, the iron source or copper source is added to a serum replacement media at a final concentration in the range of about 0.05 to 250 ng/ml, 0.05 to 100 ng/ml, from about 0.05 to 50 ng/ml, from about 0.05 to 10 ng/ml, from about 0.1 to 5 ng/ml, from about 0.5 to 2.5 ng/ml, or from about 1 to 5 ng/ml. It is further contemplated that the iron source or copper source is in a final concentration in the serum replacement of about 0.05, 0.1, 0.25, 0.35, 0.45, 0.5, 0.6, 0.7, 0.8, 1, 1.5, 2, 2.5, 3, 4, 5, 6, 7, 8, 9, or 10 ng/ml.

The final concentration described above with respect to components in the media or liquid mix of the serum replacement composition can be used as a basis for calculating the concentration of components in either a media supplement or complete media. The final concentration of the respective components in a media supplement are 10× greater those used in the serum replacement composition. The final concentration of the respective components in a complete media is 10× less than those used in the serum replacement.

With respect to the cryopreservation media, the starting concentration ranges contemplated for the serum replacement are the same as those contemplated for the cryopreservation media. However, the cryopreservation media is used without dilution or with only minimal dilution such that the final concentration of the components and the starting concentration are approximately equivalent. For example, in various embodiments for the cryopreservation media, the final concentration of pectin in cell suspension is about 0.25 to 5 g/L, 0.5 to 4 g/L, 1.5 to 3 g/L or 1 to 2 g/L.

In various embodiments, the liposome is loaded with components beneficial to cell culture. Exemplary compositions beneficial in cell culture include, but are not limited to, iron transporters, free fatty acids, growth peptides (e.g., insulin, GHK peptide comprising gly-his-lys trimer) amino acids (essential and non-essential), vitamins, trace elements antioxidants and salts. In various embodiments, it is contemplated that the liposome is loaded with additional ethanolamine and free fatty acids.

In various embodiments, the serum replacement or media supplement is added to a basic media. Standard basic media are known in the field of cell culture and commercially available. Examples of basic media include, but are not limited to, Dulbecco's Modified Eagle's Medium (DMEM), DMEM F12 (1:1), Iscove's Modified Dulbecco's Medium, Ham's Nutrient mixture F-10 or F-12, Roswell Park Memorial Institute Medium (RPMI), MCDB 131, Click's medium, McCoy's 5A Medium, Medium 199, William's Medium E, and insect media such as Grace's medium and TNM-FH.

The serum replacement and media supplement described herein are also contemplated for use in commercially available serum-free culture medias. Exemplary serum-free medias, include but are not limited to, AIM-V (Life Technologies, Carlsbad, Calif.), PER-C6 (Life Technologies, Carlsbad, Calif.), Knock-Out™ (Life Technologies), Stem-Pro® (Life Technologies), CellGro® (Corning Life Sciences—Mediatech Inc., Manassas, Va.).

Any of these media are optionally supplemented with salts (such as sodium chloride, calcium, magnesium, and phosphate), amino acids, vitamins, buffers (such as HEPES), nucleotides (such as adenosine and thymidine), antibiotics (such as gentamicin drug), trace elements (defined as inorganic compounds usually present at final concentrations in the micromolar range), antioxidants and glucose or an equivalent energy source. Any other necessary supplements may also be included at appropriate concentrations that would be known to those skilled in the art. The culture conditions, such as temperature, pH, and the like, will be apparent to the ordinarily skilled artisan.

It is contemplated that the media compositions are packaged in unit forms. In one embodiment, the media (serum replacement, media supplement, complete media or cryopreservation media) is packaged in a volume of 10 ml, 50 ml, 100 ml, 500 ml or 1 L. In a related embodiment, the serum replacement, media supplement or cryopreservation media is packaged in a 1×, 5×, 10× or 20× solution.

Cell Culture

It is contemplated that the media, e.g., serum replacement, media supplement, complete media or cryopreservation media, described herein is useful for culture of cells in vitro, preferably for cells that typically require serum supplements or defined media for adequate growth in vitro. Such cells include eukaryotic cells, such as mammalian cells, and insect cells. Mammalian cells contemplated to benefit from use of the serum replacement, complete media or media supplement include, without limitation, hamster, monkey, chimpanzee, dog, cat, cow/bull, pig, mouse, rat, rabbit, sheep and human cells. Insect cells include cells derived from *Spodoptera frugiperda* (caterpillar), *Aedes aegypti* (mosquito), *Aedes albopictus* (mosquito), *Drosophila melanogaster* (fruitfly), and *Bombyx mori*.

It is contemplated that the cells cultured with the serum replacement, complete media or media supplement, or frozen with the cryopreservation media, are immortalized cells (a cell line) or non-immortalized (primary or secondary) cells, and can be any of a wide variety of cell types that are found in vivo. Exemplary cell types include, but are not limited to, fibroblasts, keratinocytes, epithelial cells, ovary cells, endothelial cells, glial cells, neural cells, formed elements of the blood (e.g., lymphocytes, bone marrow cells), chondrocytes and other bone-derived cells, hepatocytes, pancreas cells, and precursors of these somatic cell types.

In various embodiments, the cells contemplated for use with the media are isolated from a mammalian subject. Cells isolated from a mammalian subject include, but are not limited to, pluripotent stem cells, embryonic stem cells, bone marrow stromal cells, hematopoietic progenitor cells, lymphoid stem cells, myeloid stem cells, lymphocytes, T cells, B cells, macrophages, endothelial cells, glial cells, neural cells, chondrocytes and other bone-derived cells, hepatocytes, pancreas cells, precursors of somatic cell types, and any carcinoma or tumor derived cell.

In various embodiments, the cells are a cell line. Exemplary cell lines include, but are not limited to, Chinese hamster ovary cells, including CHOK1, DXB-11, DG-44, and CHO/−DHFR; monkey kidney CV1, COS-7; human embryonic kidney (HEK) 293; baby hamster kidney cells (BHK); mouse sertoli cells (TM4); African green monkey kidney cells (VERO); human cervical carcinoma cells (HELA); canine kidney cells (MDCK); buffalo rat liver cells (BRL 3A); human lung cells (W138); human hepatoma cells (Hep G2; SK-Hep); mouse mammary tumor (MMT); TRI cells; MRC 5 cells; FS4 cells; a T cell line (Jurkat), a B cell line, mouse 3T3, RIN, A549, PC12, K562, PER.C6®, SP2/0, NS-0, U20S, HT1080, L929, hybridomas, tumor cells, and immortalized primary cells.

Exemplary insect cell lines, include, but are not limited to, Sf9, Sf21, HIGH FIVE™, EXPRESSF+®, S2, Tn5, TN-368, BmN, Schneider 2, D2, C6/36 and KC cells.

Additional cell types and cell lines are disclosed in WO 2006/004728, herein incorporated by reference. These cells include, but are not limited to, CD34+ hematopoietic cells and cells of myeloid lineage, 293 embryonic kidney cells, A-549, Jurkat, Namalwa, HeIa, 293BHK cells, HeLa cervical epithelial cells, PER-C6 retinal cells (PER.C6), MDBK (NBL-I) cells, 911 cells, CRFK cells, MDCK cells, BeWo cells, Chang cells, Detroit 562 cells, HeLa 229 cells, HeLa S3 cells, Hep-G2 cells, KB cells, LS 180 cells, LS 174T cells, NCI-H-548 cells, RPMI 2650 cells, SW-13 cells, T24 cells, WI-28 VA13, 2RA cells, WISH cells, BS-C-I cells, LLC-MK2 cells, Clone M-3 cells, 1-10 cells, RAG cells, TCMK-I cells, Y-I cells, LLC-PK1 cells, PK (15) cells, GH1 cells, GH3 cells, L2 cells, LLC-RC 256 cells, MH1C1 cells, XC cells, MDOK cells, VSW cells, TH-I, B1 cells, or derivatives thereof, fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, fibroblast and fibroblast-like cell lines), TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, MR-90 cells, MRC-5 cells, WI-38 cells, WI-26 cells, MiC11 cells, CV-I cells, COS-I cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-I1 cells, NOR-IO cells, C3H/IOTI/2 cells, HSDM1C3 cells, KLN205 cells, McCoy cells, Mouse L cells, Strain 2071 (Mouse L) cells, L-M strain (Mouse L) cells, L-MTK (Mouse L) cells, NCTC clones 2472 and 2555, SCC-PSA1 cells, NSO, NS1, Swiss/3T3 cells, Indian muntjac cells, SIRC cells, Cn cells, Jensen cells, COS cells and Sp2/0 cells, Mimic cells and/or derivatives thereof.

Cell culture conditions contemplated herein may be adapted to any culture substrate suitable for growing cells. Substrates having a suitable surface include tissue culture wells, culture flasks, roller bottles, gas-permeable containers, flat or parallel plate bioreactors or cell factories. Also contemplated are culture conditions in which the cells are attached to microcarriers or particles kept in suspension in stirred tank vessels.

Cell culture methods are described generally in the Culture of Animal Cells: A Manual of Basic Technique, 6$^{th}$ Edition, 2010 (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Other reference texts include Creating a High Performance Culture (Aroselli, Hu. Res. Dev. Pr. 1996) and Limits to Growth (D. H. Meadows et al., Universe Publ. 1974). Tissue culture supplies and reagents are well-known to one of skill and are commercially available.

It is understood that the cells are placed in culture at densities appropriate for the particular cell line or isolated cell type used with the serum replacement, complete media or media supplement. In certain embodiments the cells are cultured at $1\times10^3$, $5\times10^3$, $1\times10^4$, $5\times10^4$, $1\times10^5$, $5\times10^5$, $1\times10^6$ or $5\times10^6$ cells/ml.

In various embodiments, it is contemplated that the media described herein is used as a cryopreservation media. Cryopreservation refers to storage of cells or tissue in an environment of less than 8° C., which allows for extended storage of cells and may be at any temperature below 8° C., including temperatures at or below 4° C., 0° C., −20° C., −70° C., −135° C., or in liquid nitrogen (−196° C.). Methods for cryopreserving cells with a medium containing choline salts and sucrose is disclosed in U.S. Pat. No. 5,985,538. Additional cryopreservation compositions and methods are disclosed in U.S. Pat. Nos. 7,935,478 and 7,112,576. It is contemplated that the cryopreservation media described herein may further comprise one more of the following agents: dimethyl sulfoxide (DMSO), glycerol, ethylene glycol, polyethylene glycol, propylene glycol, sugars (such as sucrose, dextrose, trehalose, pectin), proteins, carbohydrates (such as hydroxy ethyl starch (HES)), dextran and/or polylysine. In various embodiments, the cryopreservation media comprises liposomes and/or pectin.

In various embodiments, at least 30% of the cells remain viable upon thawing when placed in a media herein, whether used as a serum replacement, media supplement or complete media. In various embodiments, viability of cells upon thaw is 40%, 50%, 60%, 65%, 70%, 75%, 80% or higher.

Additional assays to measure viability after cryopreservation include, but are not limited to, determination of colony forming units of stem cells, determination of cell doubling time and proliferation, MTT assay, resazurin assay, and other assays used in the art to measure cell viability and growth.

In various embodiments, it is contemplated that certain of the media compositions or liposome compositions as described herein promote improved culture of cells, e.g., increased cell growth, cell viability or increased expression of recombinant protein, compared to media or liposome compositions comprising a different set of components. It is contemplated that those media or liposome compositions promoting improved culture of cells are used for further experimentation.

In various embodiments, it has been demonstrated that a serum replacement media comprising a liposome having an antioxidant supports increased growth of cells in culture. This is in contrast to previous studies which show that the antioxidant vitamin E, or alpha tocopherol, suppresses growth of cells in culture.

Kits

The disclosure further provides for a kit comprising a media as described herein, e.g., a serum replacement, media supplement, complete media or cryopreservation media, and instructions for use. In various embodiments, the media is a serum replacement, media supplement or cryopreservation media and the kit provides a base media and/or additional factors useful for creating a complete media. In various embodiments, the media is packaged in a container with a label affixed to the container or included in the package that describes use of the compositions for use in vitro, in vivo, or ex vivo. Exemplary containers include, but are not limited to, a vessel, vial, tube, ampoule, bottle, flask, and the like. It is further contemplated that the container is adapted for packaging the media, e.g., serum replacement, media supplement or cryopreservation media in liquid or frozen form. It is contemplated that the container is made from material well-known in the art, including, but not limited to, glass, polypropylene, polystyrene, and other plastics. In various aspects, the compositions are packaged in a unit dosage form. The kit optionally includes a device suitable for combining the serum replacement, media supplement or cryopreservation media with a basic media, and alternatively combining the media with additional growth factors. In various aspects, the kit contains a label and/or instructions that describes use of the media for cell culture or cryopreservation.

Additional aspects and details of the present serum replacement will be apparent from the following examples, which are intended to be illustrative rather than limiting.

Example 1

Exemplary Liposome Serum Replacement Composition

Methods for making an exemplary liposome and serum replacement media contemplated herein are described below. Components useful in the serum replacement are set out in Tables 3 and 4. Components listed in the tables are not meant to be limiting, but to demonstrate the efficacy of the liposome complex in the serum replacement. Table 3 sets out exemplary components of the liposome composition. Optionally, the liposome complex can comprise Tween® (e.g., 50 uL/L).

TABLE 3

| Ingredients | concentration (per Liter) | | Example source | catalog # |
|---|---|---|---|---|
| PHOSAL ® 53 | 250 | ul | Lipoid | 368204 |
| Ethanol | 750 | ul | KOPTEC | V1016 |
| Ethanolamine | 5 | mg | Sigma | 398136 |
| Linolenic Acid | 0.1 | mg | Sigma | L2376 |
| Linoleic acid | 0.5 | mg | Sigma | L1012 |
| Cholesterol | 50 | mg | Sigma | C1231 |

To make a liposome, 700 ul of ethanol was placed into a 1.5 ml microcentrifuge tube and 250 ul of PHOSAL® 53 added to the ethanol. 50 mg of cholesterol was added to the PHOSAL® mix and heated to 50° C. until the cholesterol was in solution. The mixture was vortexed (VORTEX GENIE®, Scientific Industries Inc., Bohemia, N.Y.) on 10 for 20-30 second increments until the solution was a clear amber color (vortex briefly and place lipid mix back on heat and repeat until in solution). Optionally, 50 ul of Tween® 20 is added to the lipid mix and vortexed. Ethanolamine was added to the mixture and vortexed. Fatty acids, such as linoleic acid and linoleneic acid were then added and mixed by vortexing. The final lipid mix is stored in the dark at 4° C.

The serum replacement also comprises a base media liquid mix to be combined with the lipid mix described above. In one embodiment, the base media liquid mix comprises the following components: pectin, sodium chloride (NaCl), dextrose, potassium chloride (KCl), sodium phosphate ($Na_2HPO_4$), potassium phosphate ($KH_2PO_4$), selenium, molybdate, ferric citrate, glycerol and pluronic. An exemplary embodiment of a base liquid mix is described in Table 4.

TABLE 4

| Ingredients | concentration (per Liter) | | Example source | catalog # |
|---|---|---|---|---|
| Liquid component | | | | |
| NaCl | 8 | g | Sigma | S9888 |
| KCl | 0.2 | g | Sigma | P4504 |
| $Na_2HPO_4$ | 1.5 | g | Sigma | S0876 |
| $KH_2PO_4$ | 0.2 | g | Sigma | P5379 |
| Dextrose | 5 | g | Sigma | G6138 |
| pectin | 1 | g | Gillco (DuPont) | 413720 |
| Glycerol | 0.03 | ml | Sigma | G2025 |
| Selenium | 50 | ug | Sigma | S5261 |
| Pluronic 68 | 0.5 | g | Sigma | P1300 |
| Molybdnate | 10 | ug | Sigma | M1651 |
| Ferric Citrate | 2 | mg | Sigma | F3388 |

Dextrose, pectin and NaCl were mixed as powder and added slowly to 600 mls of double distilled water ($ddH_2O$). Potassium chloride, sodium phosphate and potassium phosphate powders were added into the pectin-NaCl solution and mixed until in solution. Selenium, molybdate and ferric citrate were diluted in phosphate buffered saline (PBS) and mixed until in solution. Glycerol was added and the solution brought to pH to 7.2 using 1N NaOH. Pluronic was added to the solution and volume brought up to 1 L with $ddH_2O$.

To combine the lipid and liquid mix, 1 mL of the lipid mix is then mixed in 10 mLs of serum replacement base liquid. The lipid mix is filtered through a low binding filter pore size (e.g., 0.22 uM). 10 mL of base media mix was placed into a sterile 100 mL container. Lipid mix was slowly dropped into 10 mL of the base media while swirling the 10 mL of base media and mixed vigorously, e.g., using a vortex and then shaking bottle. Optionally, the liposome mix is put through a microfluidizer, which will aid in making uniform sized nanoliposomes. To make a larger volume of solution, 10 ml of liposome mix is slowly dropped into 990 ml liquid mix while swirling the base media to reach 1 Liter solution.

Example 2

Liposome Serum Replacement Promotes Cell Growth and Viability

To demonstrate the ability of the serum replacement described in Example 1 to facilitate cell growth and proliferation of cells, primary cells isolated from mice or cell lines were cultured in stock media comprising serum replacement.

Figure 1:
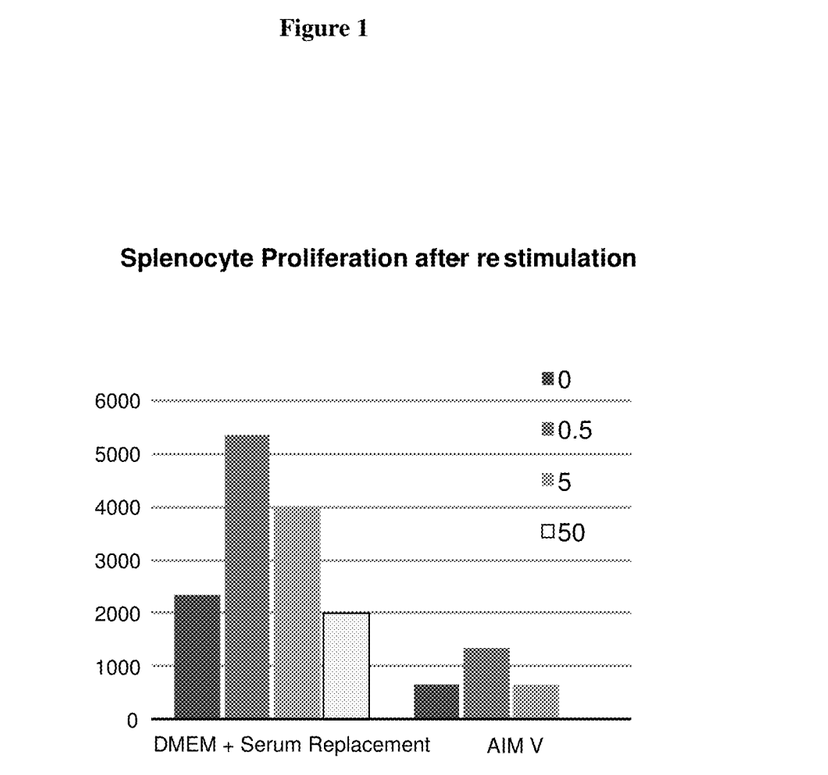
FIG. 1 illustrates the effects of the serum replacement describe herein on stimulated splenocytes compared to a commercially available, FDA approved serum-free media.
Figure 2A:
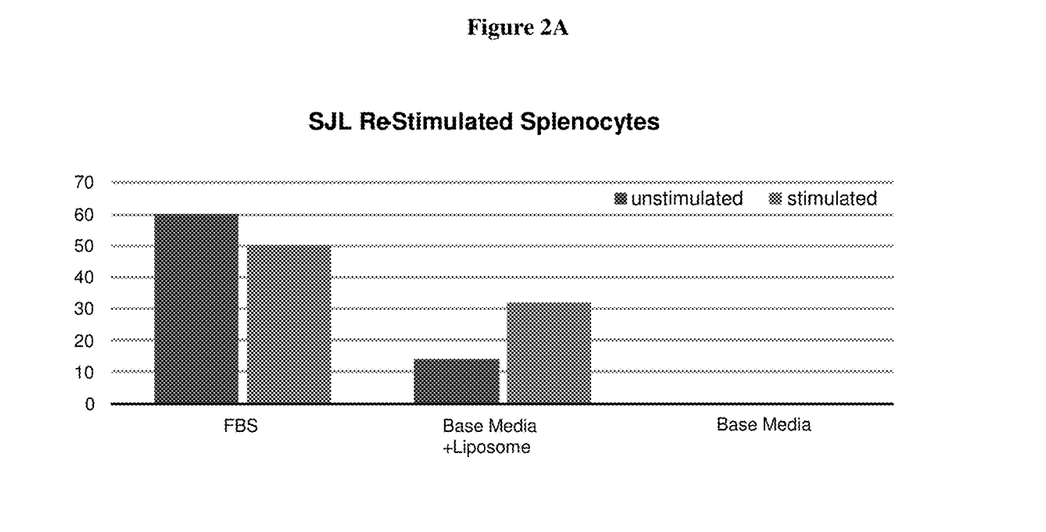
FIG. 2A and FIG. 2B illustrate the effects of the serum replacement described herein on the growth of stimulated splenocytes compared to culture of splenocytes in media comprising fetal bovine serum.
Figure 2B:
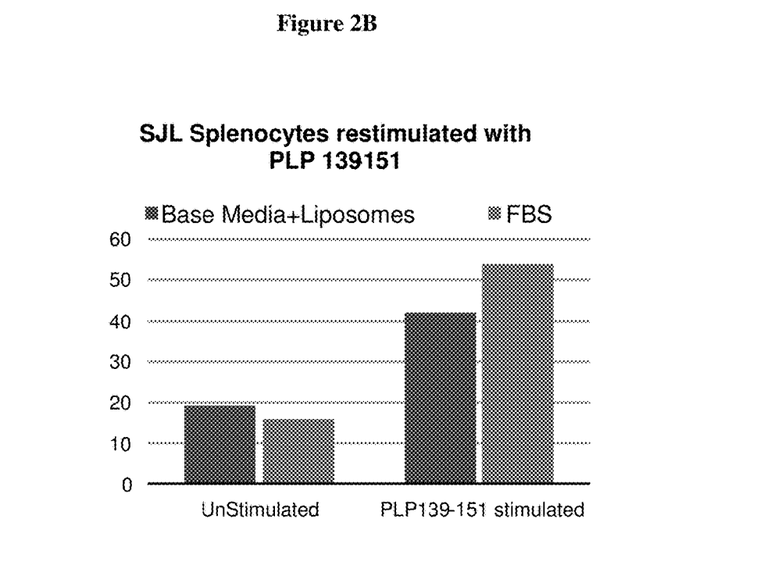

Splenocytes were isolated from SJL mice previously immunized with phospholipoprotein (PLP) 139-151 as described previously (McRae et al., J Exp Med. 182(1):75-85, 1995) and growth of cells in DMEM+10% serum replacement compared to growth in a commercially available serum free media AIM-V® (Invitrogen, Carlsbad Calif.). $5 \times 10^5$ cells were placed in a 96 well plate in 200 uL of growth media and the level of splenocyte proliferation in response to restimulation with PLP139-151 (0, 0.5, 5 or 50 ug/ml) was measured after 3 days. FIG. 1 shows that culture of cells in DMEM+10% serum replacement resulted in significantly greater proliferation than the serum-free media. Growth of splenocytes in DMEM containing FBS or DMEM+10% serum replacement was also compared. FIG. 2A shows that cells cultured in DMEM+10% FBS proliferated whether stimulated or unstimulated, resulting in a low stimulation index, while the number of splenocytes cultured in DMEM+10% serum replacement doubled. FIG. 2B represents a second proliferation assay in which the splenocytes were cultured in DMEM+10% FBS or DMEM+10% serum replacement. FIG. 2B shows that cells cultured in DMEM/10% FBS had a stimulation index above 3 whereas cells cultured in DMEM/10% serum replacement had a stimulation index slightly under 3. Interestingly, the data in FIGS. 2A and 2B shows that culture of cells in DMEM/10% serum replacement provides consistent proliferation results in contrast to culture of cells in DMEM/FBS which can result in non-specific proliferation even in unstimulated cell populations. The serum replacement described herein provides more consistent, reproducible cell culture conditions compared to culture in FBS, which can have cell-stimulatory properties and can cause cell stimulation with internal lot-to-lot variation.

In addition to primary cell culture, the effects of serum replacement on growth of cell lines was determined. Chinese hamster ovary (CHO) cells were cultured ($5 \times 10^5$ in 96 well plates) in Hams' (F12) media alone or Hams' containing 10% serum replacement and cell growth and viability was measured. The number of CHO cells cultured in Hams' media doubled at 4 days, whereas the number of CHO cells cultured in Ham's/10% serum replacement increased by approximately 8-fold at 4 days. Viability of cells in either culture condition was approximately 90% at 4 days.

It has also been demonstrated that a serum replacement media that includes a liposome comprising alpha tocopherol improves cell growth compared to a serum replacement having a liposome lacking the antioxidant. This is in contrast to reports that alpha tocopherol suppresses growth of cells in culture. See e.g., Sylvester et al., "Vitamin E inhibition of normal mammary epithelial cell growth is associated with a reduction in protein kinase C (alpha) activation" Cell Prolif. 34(6):347-57, 2001, or Neuzil et al., "Vitamin E analogues as inducers of apoptosis: implications for their potential antineoplastic role" Redox Rep. 6(3):143-51, 2001.

These results demonstrate that the serum replacement comprising the liposome described herein effectively provides for growth of cell lines in vitro.

Example 3

Liposome Serum Replacement Reduces Cell Death and Intra-Experiment Variability Compared to Serum The serum replacement described herein was also examined for its ability to slow or reduce cell death during culture using isolated CD4+ T cells.

CD4+ T cells were isolated from spleens of mice using a magnetic bead isolation protocol (see, e.g., MACS® isolation, Miltenyi Biotec Inc., Auburn, Calif. or DYNABEADS®, Life Technologies, Carlsbad, Calif.). Growth of cells in DMEM+10% serum replacement was compared to growth in DMEM comprising 10% FBS. The media comprising serum replacement was also supplemental with various growth factors to compensate for those additional growth factors found in FBS (see, e.g., U.S. Patent Publication 20130130373). $5 \times 10^5$ CD4+ T cells were placed in a 96 well plate in 200 uL of growth media and the level of T cell proliferation in response to stimulation with anti-CD3/anti-CD28 was measured via WST-1 incorporation over 3 days (see, e.g., Francoeur et al., Biochemica 3:19-25, 1996). The WST-1 assay uses cleavage of the tetrazolium salt WST-1 to a soluble formazan dye to measure cell proliferation. As the cell number increases, levels of tetrazolium reductase go up, resulting in an increase in the conversion of WST-1 to a detectable dye. The quantitation of the dye is measured by absorbance at 440 nm.

Figure 3A:
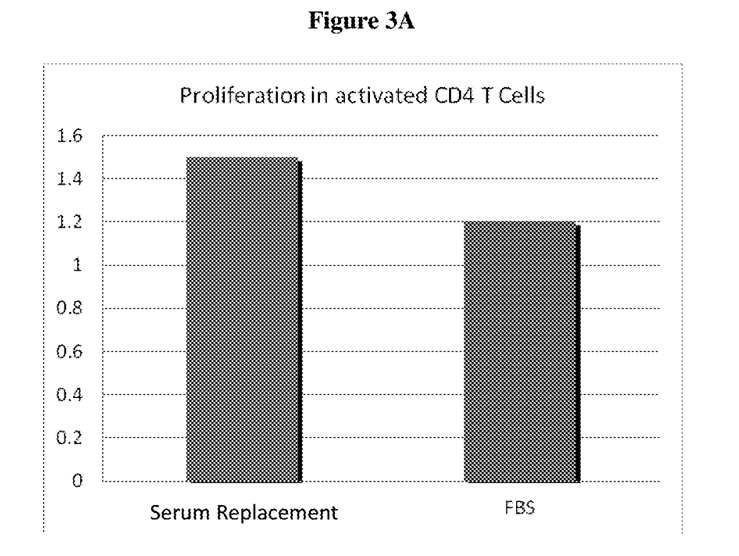
FIG. 3A shows that serum replacement plus growth factors induces cell proliferation to a greater extent than media plus FBS.
Figure 3B:
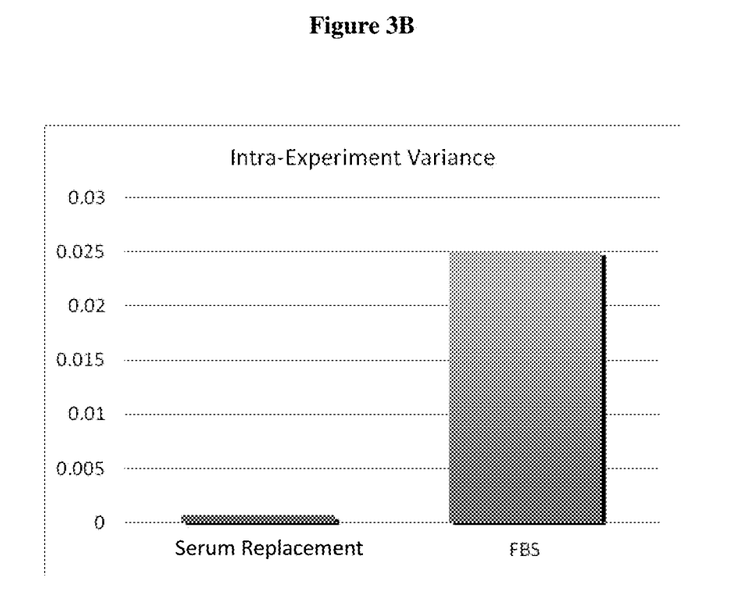
FIG. 3B illustrates that the intra-experimental variation in proliferation is reduced when cells are cultured with serum replacement compared to FBS.
Figure 4A:
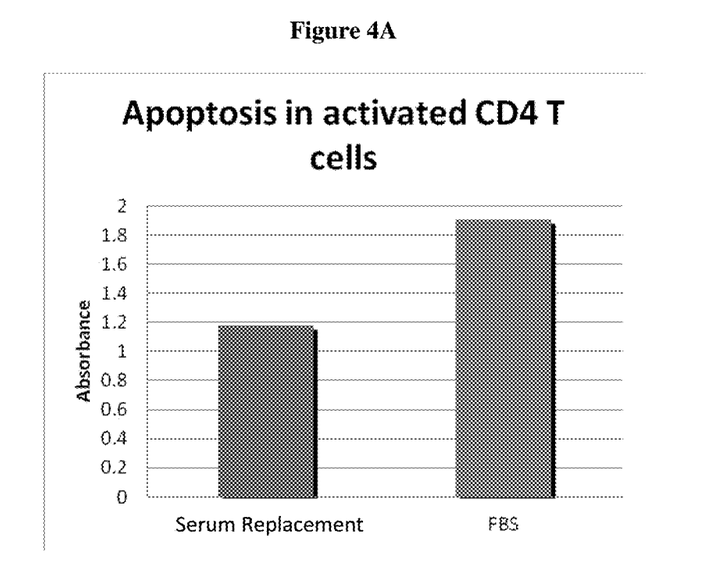
FIG. 4A shows that culture of cells in serum replacement plus growth factors reduces the level of cell death over a 3 day culture compared to cells cultured in media plus FBS.
Figure 4B:
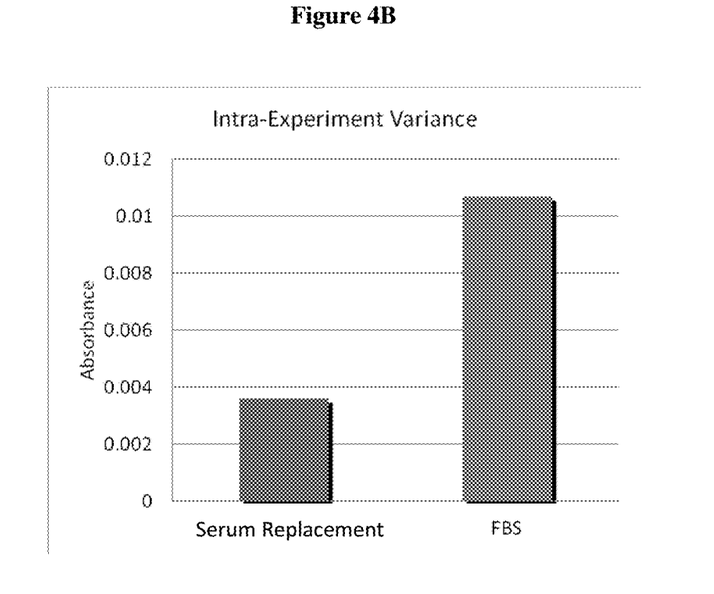
FIG. 4B illustrates that the intra-experimental variation in apoptosis is reduced when cells are cultured with media containing serum replacement compared to media comprising FBS.

FIG. 3 shows that stimulated CD4+ T cells proliferated better than or at least comparable to proliferation observed in cells cultured in medium plus FBS. Eight replicate cultures were used for each stimulation group in order that the intra-experimental variants could be calculated. Variance was determined as the square of the standard deviation observed in the proliferation. FIG. 3B shows that culture of cells in serum replacement and growth factors results in minimal intra-experimental variance compared to culture in FBS. Cell death over the course of the 3 day culture was also measured by lactate dehydrogenase (LDH) apoptosis assay (see, e.g., Wolterbeek, H. T., and van deer Meer, J. G. M., Assay Drug Dev Technol 3:675-682, 2005). The assay measures the levels of LDH in the supernatant that result from cell membrane rupture. Through a series of reactions, the LDH is leads to production of a detectable soluble dye that enables quantitation by absorbance from 490-520 nm. Higher levels of LDH indicate increased apoptosis. FIG. 4A shows that culture in media plus serum replacement and growth factors reduces the level of apoptosis taking place during culture compared to culture with FBS. FIG. 4B illustrates that the intra-experimental variance in this experiment was also minimal in cells cultured in serum replacement compared to those cultured with media containing FBS.

These results show that the serum replacement described herein, as well as the complete media or media supplement comprising liposomes, provide a cell culture environment that is comparable to growth in FBS, but that lacks the disadvantages seen in culture with FBS, such as lot-to-lot variation and intra-experimental variation.

Numerous modifications and variations in the invention as set forth in the above illustrative examples are expected to occur to those skilled in the art. Consequently only such limitations as appear in the appended claims should be placed on the invention.

What is claimed:

1. A medium for use with cells in suspension or in adherent culture, the medium comprising a base physiological buffer liquid mix and liposomes comprising cholesterol, phosphatidylcholine, and fatty acids, wherein the liposome is in an amount such that the final concentration of cholesterol in the liposome is from 10 to 200 mg/L, and wherein the final concentration of phosphatidylcholine in the liposome is from 50 mg/L to 1 g/L.

2. The medium of claim 1, wherein the liposome comprises one or more fatty acids selected from the group consisting of linolenic acid, linoleic acid, myristic acid and oleic acid.

3. The medium of claim 1, wherein the liposome further comprises ethanol amine and polysorbate.

4. The medium of claim 1, wherein the base physiological buffer liquid mix comprises one or more supplement selected from the group consisting of an organic salt, inorganic salt, buffer, iron source or iron transporter, glycerol, amino acid, vitamin, sugar, antioxidant and trace element.

5. The medium of claim 1, wherein the medium is a serum replacement, complete medium, medium supplement, or cryopreservation medium.

6. The serum replacement, complete medium, medium supplement, or cryopreservation medium of claim 5, wherein the liposome is a nanoparticle.

7. A method of culturing cells comprising culturing cells in a medium of claim 1.

8. The method of claim 7, wherein the cell is selected from the group consisting of pluripotent stem cells, embryonic stem cells, bone marrow stromal cells, hematopoietic progenitor cells, lymphoid stem cells, myeloid stein cells, T cells, B cells, macrophages, hepatic cells, pancreatic cells, carcinoma cells and cell lines.

* * * * *